US00PP28351P3

(12) United States Plant Patent
Suphachadiwong

(10) Patent No.: US PP28,351 P3
(45) Date of Patent: Aug. 29, 2017

(54) *VANDA* PLANT NAMED 'SPCDW1405'

(50) Latin Name: ***Vanda* spp.**
Varietal Denomination: SPCDW1405

(71) Applicant: Thumrong Suphachadiwong, Bangphra (TH)

(72) Inventor: Thumrong Suphachadiwong, Bangphra (TH)

(73) Assignee: Suphatchatwong Innovation Co., Ltd., Bangphra (TH)

( * ) Notice: Subject to any disclaimer, the term of this patent is extended or adjusted under 35 U.S.C. 154(b) by 61 days.

(21) Appl. No.: 14/757,062

(22) Filed: Nov. 13, 2015

(65) Prior Publication Data

US 2016/0143203 P1 May 19, 2016

(30) Foreign Application Priority Data

Nov. 14, 2014 (QZ) ..... PBR 2014/2943

(51) Int. Cl.
*A01H 5/02* (2006.01)

(52) U.S. Cl.
USPC ..... Plt./311

(58) Field of Classification Search
USPC ..... Plt./311
See application file for complete search history.

*Primary Examiner* — June Hwu
(74) *Attorney, Agent, or Firm* — Samuel R. McCoy, Jr.

(57) ABSTRACT

A new and distinct *Vanda* cultivar named 'SPCDW1405' which is characterized by the combination of a unique light blue general tonality of the flower with a pronounced tessellated color pattern of a slightly darker blue coloration, undulating sepal and petal margins, a dark violet labellum, frequent flowering, and the stability of all characteristics from generation to generation. The new variety is a *Vanda*, typically produced as an indoor ornamental plant.

3 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1405'.

CROSS REFERENCE TO RELATED APPLICATIONS

This application claims priority to the Community Plant Variety Rights application number 2014/2943, filed Nov. 14, 2014, which is herein incorporated by reference.

BACKGROUND OF THE INVENTION

Parentage: The *Vanda* variety 'SPCDW1405' originated as a naturally occurring, whole-plant mutation of *Vanda* 'Blue Magic' (unpatented in the United States, Netherlands Plant Breeder's Rights No. 020716), a variety developed and owned by the inventor. The inventor of 'SPCDW1405' is a commercial ornamental plant producer and regularly discovers mutations of *Vanda* 'Blue Magic' at his greenhouse operation in Bangphra, Thailand. For said mutations which seem to exhibit commercial potential, cuttings are taken to produce trial plants which are subsequently grown for evaluation. This process resulted in the selection of a limited number of single plants with commercial potential. Micro propagation of said plants was initiated in the laboratory of breeder and limited amounts of trial plants were grown to the flowering stage, after which the positive characteristics were evaluated again. The variety now called 'SPCDW1405' was initially discovered in February of 2009 at the inventor's greenhouse in Bangphra, Thailand, as one such mutation of 'Blue Magic'.

Asexual Reproduction: Asexual reproduction of the new cultivar 'SPCDW1405', by way of mericloning, was first initiated in April of 2009 at a commercial laboratory belonging to the inventor in Bangphra, Thailand, with the first mericlones so reproduced flowering in 2014. Access to all plants was restricted, as plants were kept in a greenhouse not open to the public, and tissue culture plantlets were in a laboratory belonging to the inventor, and not accessible to the public. Through five subsequent generations, the unique features of this cultivar have proven to be stable and true to type.

SUMMARY OF THE INVENTION

The cultivar 'SPCDW1405' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1405'. These characteristics in combination distinguish 'SPCDW1405' as a new and distinct *Vanda* cultivar:

1. *Vanda* 'SPCDW1405' exhibits a unique light blue general tonality of the flower, with a pronounced tessellated color pattern of a slightly darker blue coloration; and
2. *Vanda* 'SPCDW1405' exhibits a dark violet general tonality of the labellum; and
3. *Vanda* 'SPCDW1405' exhibits broad, concave flower petals; and 4. *Vanda* 'SPCDW1405' exhibits sepals and flower petals which are curled or twisted in a propeller fashion; and
5. *Vanda* 'SPCDW1405' exhibits a very light violet to nearly-white pedicellate ovary; and
6. *Vanda* 'SPCDW1405' flowers frequently.

BOTANICAL DESCRIPTION OF THE PLANT

Figure 1:
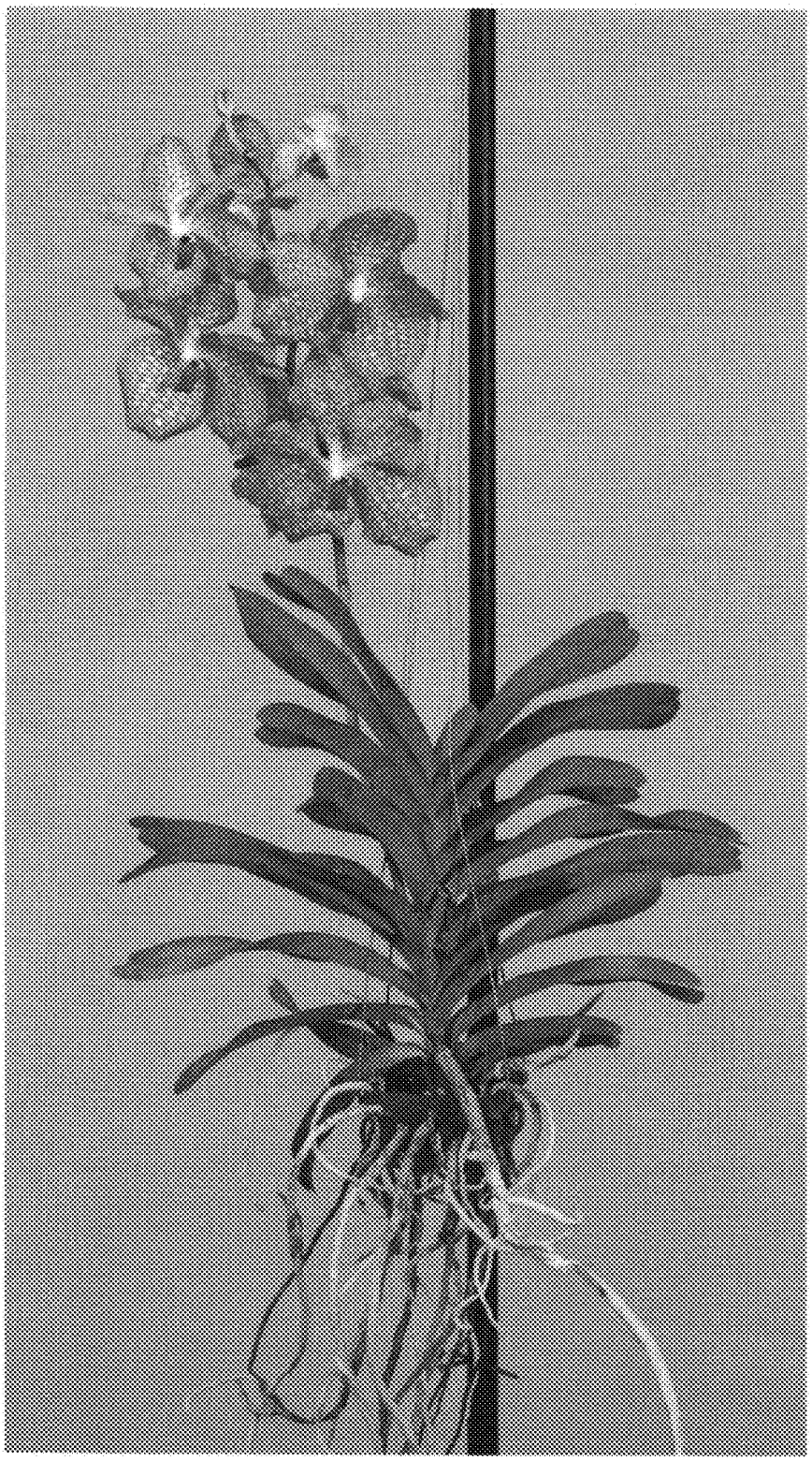
FIG. 1 illustrates, as nearly true as it is reasonably possible to make the same in color photographs of this type, an exemplary plant of 'SPCDW1405' grown in a commercial greenhouse in Honselersdijk, the Netherlands. This plant is approximately 5 years old from the time of mericloning, shown planted in an 8 by 8 cm container.
Figure 2:
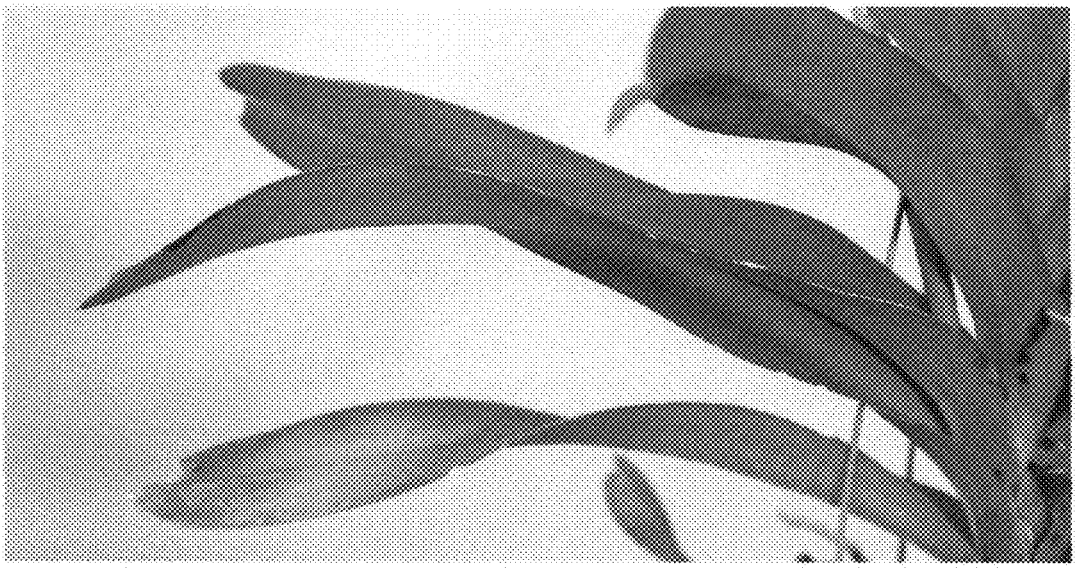
FIG. 2 illustrates, as nearly true as it is reasonably possible to make the same in color photographs of this type, the typical foliage of 'SPCDW1405'.
Figure 3:
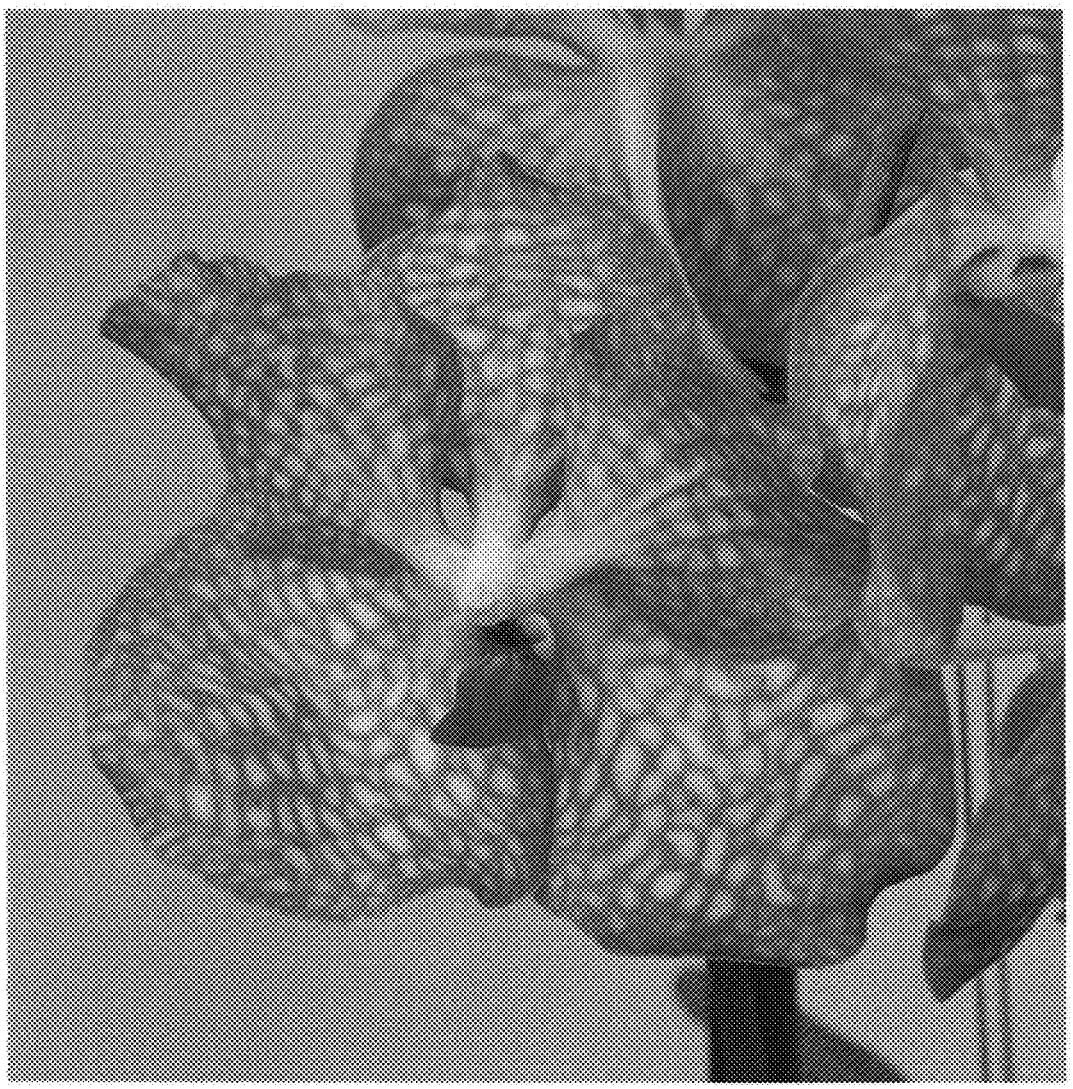
FIG. 3 illustrates, as nearly true as it is reasonably possible to make the same in color photographs of this type, the typical flowers of 'SPCDW1405'.

The following observations and measurements made in October of 2015 describe averages from a sample set of six specimens of five year-old 'SPCDW1405' plants grown in a greenhouse in Honselersdijk, the Netherlands. Temperatures ranged were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1405' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, 2015 (sixth edition).

A botanical description of 'SPCDW1405' and comparisons with other varieties of *Vanda* are provided below.

Plant description:

*Growth habit.*—Perennial; monopodial, upright. Single monopodial leafy stem, with flowers carried slightly above the leaf plane, inflorescences grow from the leaf axils.

*Average height from base (plant grown in hanging basket, so no soil line present) to top of foliage.*—32.5 cm.

*Average height from base (plant grown in hanging basket, so no soil line present) to top of flowers.*—59.2 cm.

*Plant spread.*—Average of 36.3 cm.

*Normal pot size.*—Hanging basket (8 by 8 cm, square).

*Growth rate.*—Moderate.

*Plant vigor.*—Moderate.

*Propagation type.*—Meristematic tissue culture propagation using the base of the leaves.

*Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility.*—Similar to other *Vanda* varieties.

*Environmental tolerances.*—Adapt to, at least, USDA Zones 11 and 12; high tolerance to rain; moderate to high tolerance to wind.

Root system:

*General.*—Moderately rooting; with aerial roots only.

*Dimensions, mature roots.*—48.4 cm long with a diameter of 0.5 cm, on average.

*Texture.*—Very fleshy; non-fibrous.

*Color.*—Greyed-Green, near RHS 192A to 192B; root apex is yellow-green, RHS 144B.

Stem:

*Branching habit.*—Single monopodial leafy stem.

*Number of primary (main) stems per plant.*—One.

*Number of secondary (lateral) branches per plant.*—None.

*Appearance and shape.*—Circular, formed by the leaf sheaths.

*Length.*—17.6 cm.

*Diameter.*—1.3 cm.

*Internode length.*—0.8 cm.

*Luster.*—Matte.

*Aspect.*—Near vertical.

*Strength.*—Very strong.

*Color, juvenile.*—Yellow-green, near 145B to 145C.

*Color, mature.*—Yellow-green, near 145B to 145C.

*Color at internodes.*—Yellow-green, near 145B to 145C.

*Pubescence.*—Glabrous.

Foliage:

*Arrangement.*—Distichous.

*Quantity.*—Approximately 21 leaves per plant.

*Dimensions.*—18.1 cm long and 3.1 cm wide, on average.

*Shape of blade.*—Ligulate; moderately carinate.

*Aspect.*—Slightly curved and moderately twisted.

*Apex.*—Unequal praemorse.

*Base.*—Sheathing.

*Sheath dimensions.*—1.5 cm long and 1.4 cm wide, on average.

*Sheath color.*—Yellow-Green, near RHS 145B.

*Margin.*—Entire.

*Pubescence, texture and luster of adaxial surface.*—Glabrous, smooth, and slightly glossy.

*Pubescence, texture and luster of abaxial surface.*—Glabrous, smooth, and matte.

*Color.*—Juvenile foliage, adaxial surface — Green, near RHS 143A to 143B. Juvenile foliage, abaxial surface — Green, near RHS 143B to 143C. Mature foliage, adaxial surface — Green, nearest to RHS 143A, yet darker. Mature foliage, abaxial surface — Yellow-green RHS 144A.

*Venation.*—Parallel.

*Venation color, adaxial surface.*—Green, nearest to RHS 143A, yet darker.

*Venation color, abaxial surface.*—Green, near RHS 143C.

*Petiole.*—No petioles present, leaves sessile.

Inflorescence:

*Inflorescence arrangement*.—Axially placed raceme.

*Natural flowering season*.—Autumn into winter.

*Inflorescence quantity*.—One.

*Flowers per inflorescence*.—Average of 8 open flowers and 1 unopened flower bud.

*Inflorescence height*.—Approximately 26.0 cm (measured from base of lowest flower to top of upper flower).

*Inflorescence diameter*.—Approximately 21.1 cm.

*Peduncle*.—Dimensions — Approximately 45.3 cm long and 0.6 cm wide. Aspect — Approximately 25° angle to lateral branch axis. Strength — Moderately strong. Texture and luster — Glabrous and moderately glossy. Color — Yellow-green, near RHS 144B.

Bud:

*Length*.—Average of 1.5 cm.

*Diameter*.—Average of 1.1 cm.

*Shape*.—Broad obovate.

*Pubescence, texture and luster*.—Glabrous, smooth and moderately glossy.

*Color*.—Yellow-green, near RHS 145B; apex and immature spur are tinged with purple, near N77D.

Flower:

*Flower type*.—Zygomorphic (orchidaceous), typical shape for the genus *Vanda*.

*Flowering habit*.—Moderate.

*Shape*.—Zygomorphic, single; consisting of three sepals and three petals, one of which is transformed into a labellum; the two lateral petals moderately to heavily overlap the dorsal sepal and the lateral sepals; lateral sepals are touching; dorsal sepal is free of the lateral sepals.

*Aspect*.—Flowers are outward-facing to slightly nodding.

*Height*.—Approximately 12.3 cm.

*Diameter*.—Approximately 12.5 cm.

*Depth*.—Approximately 5.6 cm.

*Fragrance*.—No fragrance.

*Lastingness*.—3 weeks.

*Persistent*.—Self-cleaning.

*Petals*.—Quantity of Petals — 3; two conventional petals and one labellum. Arrangement — One lateral petal on each side. Length — Approximately 6.1 cm. Width — Approximately 5.4 cm. Shape — Broad ovate to near orbicular. Apex — Obtuse. Base — Cuneate. Margin — Entire; moderately undulate. Pubescence, texture and luster of upper surface — Glabrous, velvety and matte. Pubescence, texture and luster of lower surface — Glabrous, velvety and matte. Color when opening, upper surface — White, near RHS NN155D; apex is violet, near RHS N87D. Color when opening, lower surface — White, near RHS NN155D; apex is violet, near RHS N87D. Color when fully opened, upper surface — White, near RHS NN155C. Color when fully opened, lower surface — White, near RHS NN155C. Fading, upper surface — Not fading. Fading, lower surface — Not fading. Venation color, fully opened, upper surface — Violet to violet-blue, near N88B and 90B to 90C. Venation color, fully opened, lower surface — Violet, in between near N88B and N88C.

*Labellum*.—Shape — Three-lobed; the shape of the lateral lobes is broad ovate and the aspect is involute; the central lobe is near rhombic and the aspect is revolute. Length — Central lobe — Approximately 2.3 cm. Lateral lobes — Approximately 1.0 cm. Width — Central lobe — Approximately 1.3 cm. Lateral lobes — Approximately 0.7 cm. Apex — Central lobe — Emarginate. Lateral lobes — Unequally emarginated. Base — Central lobe — Cuneate. Lateral lobes — Cuneate. Margin — Entire; central lobe moderately undulate and lateral lobes not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte. Lateral lobes — Glabrous, velvety, and matte. Color when opening, upper surface — Central lobe — Violet, near N87A. Lateral lobes — White, near RHS NN155C; tinged with greyed-purple, near RHS 186D, with a small yellow dot, near RHS 12B. Color when opening, lower surface — Central lobe — Violet, near RHS N87A; fading to white RHS N155A towards the base. Lateral lobes — White, near RHS NN155A; tinged with purple towards the apex, near RHS 76C; based is purple, RHS N78A. Color when fully opened, upper surface — Central lobe — Violet, in between near RHS N87A and N88A, yet darker. Lateral lobes — White, near RHS NN155C; tinged with purple, near RHS 76C; base is purple, near RHS N78A, with a small yellow dot, near RHS 12B. Color when fully opened, lower surface — Central lobe — Violet, in between near RHS N87A and N88A; closest to N87A. Lateral lobes — White, near RHS NN155A. Fading, upper surface — Not fading. Fading, lower surface — Not fading. Venation color, fully opened, upper surface — Central lobe — Violet, in between near RHS N87A and N88A, yet darker. Lateral lobes — White, near RHS NN155C; tinged with purple, near RHS 76C. Venation color, fully opened, lower surface — Central lobe — Violet, in between near RHS N87A and N88A; closest to N87A. Lateral lobes — White, near RHS NN155A.

*Spurs*.—Quantity — Average of 1. Length — Approximately 1.0 cm. Diameter — Approximately 0.4 cm. Vertical height — Approximately 0.7 cm, at the base. Shape — Short triangular. Apex — Bluntly acute. Base — Broad Cuneate. Pubescence, texture and luster — Glabrous, smooth, and matte. Color — Violet-blue, near RHS 91 D; violet, near RHS N88C to N88D, towards the apex.

*Sepals*.—Quantity — Average of 3 unfused sepals. Arrangement — One dorsal sepal and two lateral sepals. Length — Dorsal sepal — Approximately 6.5 cm. Lateral sepals — Approximately 7.0 cm. Width — Dorsal sepal — Approximately 5.8 cm. Lateral sepals — Approximately 7.1 cm. Shape — Dorsal sepal — Broad ovate. Lateral sepals — Near orbicular. Apex — Obtuse. Base — Cuneate. Margin — Entire and slightly to moderately undulate. Pubescence, texture and luster — Glabrous, velvety, and matte. Color when opening, upper surface — White, near RHS NN155D; apex is violet, near RHS N87D. Color when opening, lower surface — White, near RHS NN155D; apex is violet, near RHS N87D. Color when fully opened, upper surface — White, near RHS NN155C. Color when fully opened, lower surface — White, near RHS NN155C. Fading, upper surface — Not fading. Fading, lower surface — Not fading. Venation color, fully opened, upper surface — Dorsal sepal — Violet, near RHS N88B. Lateral sepal — Violet to violet-blue, near in between RHS N88B and 90C. Venation color, fully opened, lower surface — Dorsal sepal — Violet, near RHS N88B. Lateral sepal — Violet to violet-blue, near in between RHS N88B and 90C.

*Pedicels*.—Length — Approximately 6.2 cm. Diameter — Approximately 0.5 cm. Angle — Approximately 50° angle to peduncle axis. Strength — Moderate. Texture — Glabrous, axially angled with 5 "ribs", axially twisted (due to resupination). Luster — Glossy. Color — White, RHS NN155C.

*Bract*.—Quantity — One bract present at the base of each pedicel. Shape — Deltoid; folded around the base of the pedicel. Dimensions — Average of 1.5 cm long and 2.3 cm wide. Apex — Broad acute. Base — Broad Cuneate. Margins — Entire. Color, both surfaces — Yellow-green, near RHS N144A.

Reproductive organs:

*Column*.—Length — Approximately 0.7 cm. Diameter — Approximately 0.7 cm. Color — White RHS NN155D.

*Ovary*.—Position — Inferior. Diameter — Approximately 0.2 cm. Color — Yellow-green RHS 150D.

*Pollinia color*.—Yellow-orange RHS 14A.

Seed and fruit: No fruit and seed production has been detected to date.

COMPARISONS WITH THE PARENT PLANT

Plants of the new cultivar 'SPCDW1405' are similar to the parent, *Vanda* 'Blue Magic', in most horticultural characteristics. However 'SPCDW1405' differs from the parent in the following characteristics:

1. The flowers of 'SPCDW1405' exhibit a light blue general tonality, whereas the flowers of 'Blue Magic' exhibit a dark blue general tonality.
2. 'SPCDW1405' exhibits dark violet general tonality of the labellum, whereas 'Blue Magic' exhibits a darker violet general tonality of the labellum.
3. 'SPCDW1405' exhibits a very light violet to nearly-white pedicellate ovary, whereas 'Blue Magic' exhibits a light violet ovary.

COMPARISON WITH THE MOST SIMILAR *VANDA* CULTIVAR KNOWN TO THE INVENTOR

'SPCDW1405' is similar in many horticultural characteristics to the commercial variety *Vanda* 'SPCDW1103' (U.S. Plant Pat. No. 25,029). However 'SPCDW1405' differs from 'SPCDW1103' in the following characteristics:

1. The sepals and petals of 'SPCDW1405' exhibit a light blue tessellation pattern against a very light violet to nearly-white background, whereas the sepals and petals of 'SPCDW1103' exhibit a very light blue tessellation pattern contrasted against a greyish-white background.
2. The tessellated color pattern on the sepals and petals of 'SPCDW1405' is very pronounced, whereas the tessellation of 'SPCDW1103' is inconspicuous.
3. 'SPCDW1405' exhibits a darker violet general tonality of the labellum, when compared to the lighter violet general tonality of the 'SPCDW1103' labellum.
4. The flower petals of 'SPCDW1405' are broader than the petals of 'SPCDW1103'.
5. The flower petals of 'SPCDW1405' are concave, whereas the petals of 'SPCDW1103' are flat.
6. The sepals and petals of 'SPCDW1405' are curled or twisted in a propeller fashion, whereas 'SPCDW1103' exhibits less of said curling.
7. The sepals and petals of 'SPCDW1405' exhibit a lesser degree of overlapping when compared to the sepals and petals of 'SPCDW1103'.

That which is claimed is:

1. A new and distinct variety of *Vanda* plant named 'SPCDW1405', substantially as described and illustrated herein.

* * * * *